(12) United States Patent
Carew et al.

(10) Patent No.: US 6,831,046 B2
(45) Date of Patent: Dec. 14, 2004

(54) HAIR CONDITIONING COMPOSITIONS IN STICK OR BAR FORM CONTAINING CATIONIC SURFACTANT AND FATTY ALCOHOL

(75) Inventors: Peter Simon Carew, Bebington (GB); Reginald Manley, Bebington (GB); Stephen Lee Wire, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 177 days.

(21) Appl. No.: 10/174,295

(22) Filed: Jun. 18, 2002

(65) Prior Publication Data

US 2003/0008790 A1 Jan. 9, 2003

(30) Foreign Application Priority Data

Jun. 22, 2001 (EP) ............................................. 01305458

(51) Int. Cl.$^7$ ................................................. C11D 1/62
(52) U.S. Cl. ....................... 510/120; 510/119; 510/122; 510/123; 510/124; 510/141; 510/440; 510/447; 510/504
(58) Field of Search .................................. 510/119, 120, 510/122, 123, 124, 141, 440, 447, 504

(56) References Cited

U.S. PATENT DOCUMENTS

| | | | | |
|---|---|---|---|---|
| 4,149,551 A | * | 4/1979 | Benjamin et al. | 132/200 |
| 4,206,196 A | * | 6/1980 | Davis | 424/401 |
| 4,344,446 A | | 8/1982 | Ehrhardt | |
| 4,510,952 A | * | 4/1985 | Gikas | 132/221 |
| 5,824,296 A | | 10/1998 | Dubief et al. | |
| 5,849,280 A | * | 12/1998 | Rechelbacher et al. | 424/70.11 |

FOREIGN PATENT DOCUMENTS

| | | |
|---|---|---|
| EP | 0 395 332 A1 | 10/1990 |
| EP | 0823252 A2 | 2/1998 |
| WO | 97/12584 | 4/1997 |
| WO | 00/74643 A1 | 12/2000 |
| WO | 00/78280 A1 | 12/2000 |

* cited by examiner

Primary Examiner—Charles Boyer
(74) Attorney, Agent, or Firm—Milton L. Honig

(57) ABSTRACT

This invention relates to a hair conditioner composition in solid form comprising at least 5 wt % cationic surfactant and at least 5 wt % fatty alcohol material, wherein the composition contains less than 80 wt % water.

15 Claims, No Drawings

HAIR CONDITIONING COMPOSITIONS IN STICK OR BAR FORM CONTAINING CATIONIC SURFACTANT AND FATTY ALCOHOL

FIELD OF THE INVENTION

The present invention relates to hair conditioning compositions with sufficient rigidity to sustain their own shape. The usual form of such compositions is a stick or bar.

BACKGROUND AND PRIOR ART

Most individuals buy and use a hair shampoo for its cleansing properties. In addition to having clean hair, a consumer also desires sufficiently-conditioned hair that, for example, is easy to comb when wet, feels smooth and does not fly away. However, hair shampoos are generally formulated with highly effective anionic surfactants that primarily clean as opposed to condition the hair. Anionic surfactants not only remove the dirt and soil from the hair, but also remove sebum naturally present on the surface of the hair fibres. Shampoos also do not disentangle wet hair and do not impart residual conditioning benefits to dry hair, such as manageability or stylability.

Therefore, the desirable cleansing properties of shampoo compositions imparted by the anionic surfactants, nonionic surfactants or amphoteric surfactants, or mixtures thereof, have the disadvantage that they tend to leave the hair in a cosmetically-unsatisfactory condition. This has resulted in the use of separate conditioning compositions, typically applied separately from the shampoo, to improve these undesirable physical characteristics. Typically, after washing the hair with shampoo and rinsing, a conditioner composition is applied to the hair for a period of time and then rinsed off. Problems such as wet combing are solved by treating the shampooed hair with a conditioner composition that coats the hair shaft and causes the individual hair shafts to resist tangling and matting because of the conditioner residue retained on the shaft.

Typically, conditioning compositions are in the form of liquids or cream-like emulsions or lotions which are applied to the hair, left for a period of time on the hair and then rinsed out. A problem associated with such liquid compositions is that the more liquid the compositions, the harder it is to hold them in the hands and the harder it is to measure them out, i.e. compositions tends to escape through the fingers. Moreover, the more liquid these compositions, the more liable they are to escape from their packaging, for example during transport and when the consumer is going on holiday.

As a result, conditioner compositions have been formulated in solid form, i.e. a form in which they are capable of maintaining a predetermined shape without the aid of any external structure. Such solid conditioner forms have the advantages of requiring a lesser amount of packaging because they are more concentrated and also of being smaller more handy products to transport.

Solid sticks are used as the delivery form for many types of cosmetic products such as deodorants, lip conditioners, and colour cosmetics. Stick formulas are generally based on either silicones, glycols and soap, or waxes. The glycol/soap base, which is water soluble or dispersible, is the traditional form for deodorants and antiperspirants. It consists primarily of water, glycols (such as glycerin or propylene glycol), alcohol and/or glycol esters, and is made into a solid form by addition of soap, usually sodium stearate.

WO97/12584 (Estee Lauder) describes a solid silicone composition comprising a 3–20 wt % polyethylene solidifying agent having an average molecular weight of less than 1000, and 20–97 wt % of a non-volatile silicone fluid. The compositions additionally comprise other pharmaceutically or cosmetically acceptable materials which are soluble in or compatible with the silicone fluid, e.g. colourants, oils, fragrances, sunscreens. The compositions can be applied to the hair or skin.

U.S. Pat. No. 4,344,446 (Bjurman & Babcock) describes a hair care package comprising a scalp cleanser in solid form and a cleaning and conditioning shampoo typically in the form of a liquid gel. The solid scalp cleanser contains a soap, an amphoteric surfactant, an antimicrobial agent and a waxy emulsifier, such as polyoxyethylene fatty alcohol ethers or high molecular weight fatty acid mono- or di-esters of polyethylene glycol, to provide rigidity to the composition.

Solid compositions based on waxy materials tend to have an undesirable greasiness to them. In addition, it is also difficult to incorporate hydrophilic active agents to such compositions and it can be difficult to rinse then out of the hair.

Consequently, other structuring agents have been looked at. EP 823,252 (A-Veda Corporation) describes cosmetic hair conditioning compositions in solid form containing a film-forming polymer and a cosmetically acceptable vehicle. The gel forming agent used to provide structure to the solid forms is a soap. However, the compositions also preferably include a nonionic surfactant, a polyhydric aliphatic alcohol, a sugar and a lower alcohol.

Attempts have increasingly been made to obtain solid compositions comprising higher concentrations of an aqueous phase. Typically such compositions are gels made from a combination of hydrophilic gelling agent and water. These have the disadvantage that they tend to be brittle and easily broken in use.

One way of addressing this problem has been to include particulate filler/structuring material in the compositions to add rigidity.

U.S. Pat. No. 5,824,296 (L'Oreal) describes a solid hair composition, which may be a conditioner, containing a particulate structuring agent. The particles are preferably of low density and hollow particles and are capable of being washed out of the hair by rinsing. Suitable particles are made from glass or thermoplastic materials such as nylon, polymers or copolymers of acrylonitrile, vinylidene chloride etc. Example 11 is a conditioner comprising 0.8 wt % behenyltrimonium chloride, 4 wt % of a cationic silicone emulsion, 8 wt % EXPANCEL particles, and over 85 wt % water. The EXPANCEL particles are hollow deformable particles of an expanded copolymer of vinylidene chloride/acrylonitrile/methacrylate.

WO 00/78280 (L'Oreal) describes solid cosmetic compositions which contain an continuous aqueous phase comprising a hydrophilic gelling agent and a lamellar filler. The compositions have a hardness which provides both easy disintegration and good stick adhesion. The compositions are primarily directed at use on the skin, either directly or via a sponge and reportedly provide freshness on application and a homogeneous coating.

There are several problems associated with the use of particulate materials in hair conditioner formulations including possible negative effects on the conditioning performance and the added expense of having to include an ingredient not normally present in a conventional hair conditioner formulation.

In conclusion, the solid hair conditioner formulations of the prior art require the use of additional components not generally present in conventional hair conditioner compositions in order to provide structure/rigidity to the compositions. This leads to disadvantages as discussed above.

Surprisingly, we have now found that hair conditioner compositions in solid form can be prepared without the need for additional structuring aids by simply lowering the water content of a conventional conditioner formulation.

The hair conditioning solid the present invention improves upon the prior art by providing a composition which is cheap, i.e. it does not require any specialised structuring agents, is easily rinsed from the hair and has a hardness which allows it to be readily applied to the hair whilst maintaining its shape. In addition, because essentially the same formulation is used as in a conventional liquid conditioner apart from the level of water, it is possible to manufacture solid and liquid forms of product on the same site which gives a considerable saving in production cost.

DEFINITION OF THE INVENTION

Accordingly, this invention provides a hair conditioner composition in solid form comprising (i) at least 5 wt % cationic surfactant, and
(ii) at least 5 wt % fatty alcohol material wherein the composition contains less than 80 wt % water.

Additionally, this invention provides for use of hair conditioner compositions in solid form as described above for conditioning the hair.

DETAILED DESCRIPTION AND PREFERRED EMBODIMENTS

Definitions

Unless specified otherwise, all wt % values quoted hereinafter are percentages by weight based on total weight of the solid conditioner composition.

Conditioner Compositions

Compositions of the invention are formulated as conditioners for the treatment of hair (typically after shampooing) and subsequent rinsing.

Conditioning Surfactant

The conditioner compositions of the present invention comprise one or more conditioning surfactants which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the general formula:

$$[N(R_5)(R_6)(R_7)(R_8)]^+(X)^-$$

in which $R_5$ is a hydrocarbyl chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in conditioner compositions of the invention include:

(i) lauryl trimethylammonium chloride (available commercially as Arquad C35 ex-Akzo); cocodimethyl benzyl ammonium chloride (available commercially as Arquad DMCB-80 ex-Akzo)
(ii) compounds of the general formula:

$$[N(R_1)(R_2)((CH_2CH_2O)_xH)((CH_2CH_2O)_yH)]^+(X)^-$$

in which:

x+y is an integer from 2 to 20;
$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;
$R_2$ is a $C_1$–$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-2 oleamonium chloride (available as Ethoquad 0/12 PG ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the general formula:

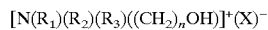

[N(R$_1$)(R$_2$)(R$_3$)((CH$_2$)$_n$OH)]$^+$(X)$^-$ in which:
n is an integer from 1 to 4, preferably 2;
R$_1$ is a hydrocarbyl chain having 8 to 14, preferably 12 to 14, most preferably 12 carbon atoms;
R$_2$ and R$_3$ are independently selected from C$_1$–C$_3$ alkyl groups, and are preferably methyl, and
X is a salt-forming anion such as those selected from halogen, (e.g. chloride, bromide), acetate, citrate, lactate, glycolate, phosphate nitrate, sulphate, and alkylsulphate radicals.
Suitable examples are lauryldimethylhydroxyethylammonium chloride (available commercially as Prapagen HY ex-Clariant).
Mixtures of any of the foregoing cationic surfactants compounds may also be suitable.
Examples of suitable cationic surfactants include:
quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, di-hardened tallow dimethylammonium chloride, distearyldimethylammonium chloride, PEG-2 oleamonium chloride, behenyltrimonium chloride and the corresponding salts thereof, e.g., bromides, hydroxides. Cetylpyridinium chloride or salts thereof, e.g., chloride Quaternium -5 Quaternium -31 Quaternium -18 and mixtures thereof.
In the conditioners of the invention, the level of cationic surfactant is at least 5, preferably at least 8, more preferably at least 10, and yet more preferably at least 12 wt %. The level of cationic can be as high as 15 wt % or greater. Typically, the level of cationic surfactant is no more than 25 wt % and preferably no more than 20 wt %.

Fatty Alcohol Material

The conditioner compositions of the invention additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 22. Examples of suitable fatty alcohols include cetyl alcohol, stearyl alcohol, behenyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is at least 5, preferably at least 10, more preferably at least 15 and yet more preferably at least 20 wt %. The level of fatty alcohol material may be as high as 40 wt % or even greater. Typically, the level of fatty alcohol material is no more than 65 wt % and preferably no more than 60 wt %.

The weight ratio of fatty alcohol material to cationic surfactant in the conditioner compositions of the invention is suitably from 10:1 to 1:10, preferably from 8:1 to 1:4, more preferably from 7:1 to 1:1, yet more preferably from 5:1 to 2:1, for example 3:1.

Water Content

The conditioner compositions of the invention comprise less than 80 wt % water. Preferably, the composition of the invention comprise less than 75, more preferably less than 70, yet more preferably less than 60 and most preferably less than 50 wt % water.

The conditioner compositions of the invention may also contain additional solvents. Suitable additional solvents include, but are not limited to, alcohols and oils. Suitable oils include silicone oils, in particular volatile silicone oils such as, for example, decamethyl pentasiloxane.

Optional Ingredients

Compositions of this invention may contain any other ingredients normally used in conditioner formulations. These other ingredients may include additional conditioning agents, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 25 wt %, preferably of up to 15 wt %, and more preferably of up to 10 wt % of the total composition.

Cationic Polymers

The compositions according to the present invention may comprise a cationic polymer for enhancing conditioning performance of the conditioner.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT, 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides(as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

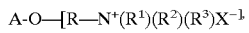

A-O—[R—N⁺(R¹)(R²)(R³)X⁻¹ wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581), A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 25, preferably from 0.1 to 5, more preferably from 0.3 to 2.5 wt %.

Structuring Agents

The compositions of the present invention may also comprise a structuring agent. Suitable structuring agents are well known to the skilled person and include, for example, insoluble particulates/fillers, gelling agents, waxes, fatty materials and polymeric systems.

Suitable polymeric structurants include polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters and heteropolysaccharide gums.

Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Suitable fatty materials and waxes include crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives.

In the context of the present invention, structuring agents are most useful in those compositions containing higher levels of water. However, an advantage of present invention is that conditioner compositions can be made in solid form without the need for excessive levels of structurants.

Preferably, the compositions of the present invention contain less than 10, more preferably less than 5, and yet more preferably less than 3 wt % of a structuring agent.

In a preferred embodiment, the compositions of the present invention are substantially free of structuring agents.

Conditioning Agents

The compositions of the present invention provide as good conditioning performance, if not better, as conventional liquid conditioners. However, the compositions may also contain one or more additional conditioning agents selected from silicone conditioning agents and non-silicone oily conditioning agents to further boost the conditioning action.

When conditioning agent is present in the compositions of the present invention in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

The compositions of the invention may contain droplets of a silicone conditioning agent for enhancing conditioning performance. The silicone is insoluble in the aqueous matrix of the composition and so is present in an "emulsified" form, with the silicone present as dispersed droplets.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself is typically at least 10,000 cst. In general we have found that conditioning performance increases with increased viscosity. Accordingly, the viscosity of the silicone itself is preferably at least 60,000 cst, most preferably at least 500,000cst, ideally at least 1,000,000 cst. Preferably the viscosity does not exceed $10^9$ cst for ease of formulation. Emulsified silicones for use in the conditioner compositions of the invention will typically have an average silicone droplet size in the composition of leas than 30, preferably less than 20, more preferably less than 10 µm. We have found that reducing the droplet size generally improves conditioning performance. Most preferably the average silicone droplet size of the emulsified silicone in the composition is less than 2 µm, ideally it ranges from 0.01 to 1 µm. Silicone emulsions having an average silicone droplet size of ≦0.15 µm are generally termed microemulsions.

Suitable silicone emulsions for use in the invention are also commercially available in a pre-emulsions form which can simply be incorporated into the base conditioner formulation during manufacture of the solid conditioner compositions.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in the conditioners of the invention are amino functional silicones. By "amino functional silicone" is meant a silicone containing at least one primary, secondary or tertiary amine group, or a quaternary ammonium group.

Examples of suitable amino functional silicones include:

(i) polysiloxanes having the CTFA designation "amodimethicone", and the general formula:

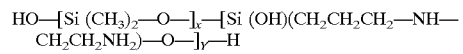

in which x and y are numbers depending on the molecular weight of the polymer, generally such that the molecular weight is between about 5,000 and 500,000.

(ii) polysiloxanes having the general formula:

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R'is a monovalent radical of formula $-C_qH_{2q}L$ in which q is a number from 2 to 8 and L is an aminofuctional group selected from the following:

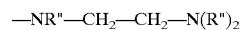

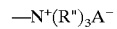

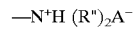

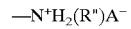

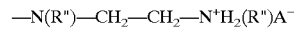

in which R" is selected from H, phenyl, benzyl, or a saturated monovalent hydrocarbon radical, e.g. $C_{1-20}$ alkyl, and A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

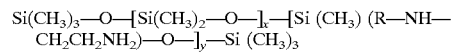

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula

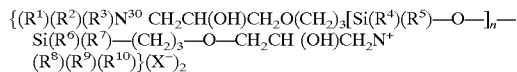

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ thru $R^9$ may be the same or different and may be independently selected from H, straight or branched chain lower alk(en)yl, and $C_5$–$C_8$ cyclic ring systems;

n is a number within the range of about 60 to about 120, preferably about 80, and $X^-$ is preferably acetate, but may instead be for example halide, organic carboxylate, organic sulphonate or the like, Suitable quaternary silicone polymers of this class are described-in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole % most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with nonionic and/or cationic surfactant.

Suitably such pre-formed emulsions will have an average amino functional silicone droplet size in the shampoo composition of less than 30, preferably less than 20, more preferably less than 10 µm. Again, we have found that reducing the droplet size generally improves conditioning performance. Most preferably the average amino functional silicone droplet size in the composition is less than 2 µm ideally it ranges from 0.01 to 1 µm.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

For compositions according to the invention intended for the treatment of "mixed" hair (i.e. greasy roots and dry ends), it is particularly preferred to use a combination of amino functional and non-amino functional silicone in compositions of the invention, especially when these are in the form of shampoo compositions. In such a case, the weight ratio of amino functional silicone to non-amino functional silicone will typically range from 1:2 to 1:20, preferably 1:3 to 1:20, more preferably 1:3 to 1:8.

The total amount of silicone incorporated into compositions of the invention depends on the level of conditioning desired and the material used. A preferred amount is from 0.01 to 50 wt % although these limits are not absolute. The lower limit is determined by the minimum level to achieve conditioning and the upper limit by the maximum level to avoid making the hair unacceptably greasy.

We have found that a total amount of silicone of from 0.5 to 25, preferably 1.0 to 15 wt % is a suitable level.

The viscosity of silicones and silicone emulsions can be measured by means of a glass capillary viscometer as set out further in Dow Corning Corporate Test Method CTM004, Jul. 20 1970.

Non-silicone Oily Conditioning Components

Compositions according to the present invention may also comprise a dispersed, nonvolatile, water-insoluble oily conditioning agent.

The oily conditioning agent will be dispersed in the composition in the form of droplets, which form a separate, discontinuous phase from the aqueous, continuous phase of the composition. In other words, the oily conditioning agent will be present in the shampoo composition in the form of an oil-in-water emulsion.

By "insoluble" is meant that the material is not soluble in water (distilled or equivalent) at a concentration of 0.1% (w/w), at 25° C.

Suitably, the $D_{3,2}$ average droplet size of the oily conditioning component is at least 0.4, preferably at least 0.8, and more preferably at least 1 µm. Additionally, the $D_{3,2}$ average droplet size of the oily conditioning component is preferably no greater than 10 more preferably no greater 8, more preferably no greater than 5, yet more preferably no greater than 4, and most preferably no greater than 3.5 µm.

The oily conditioning agent may suitably be selected from oily or fatty materials, and mixtures thereof.

Oily or fatty materials are preferred conditioning agents in the shampoo compositions of the invention for adding shine to the hair and also enhancing dry combing and dry hair feel.

Preferred oily and fatty materials will generally have a viscosity of less than 5 Pa.s, more preferably less than 1 Pa.s, and most preferably less than 0.5 Pa.s, e.g. 0.1 Pa.s and under as measured at 25° C. with a Brookfield viscometer (e.g. Brookfield RV) using spindle 3 operating at 100 rpm.

Oily and fatty materials with higher viscosities may be used. For example, materials with viscosities as high as 65 Pa.s may be used. The viscosity of such materials (i.e. materials with viscosities of 5 Pa.s and greater) can be measured by means of a glass capillary viscometer as set out further in Dow Corning Corporate Test Method CTM004, Jul. 20 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid eaters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$–$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.2 to 25, preferably from 0.5 to 20, more preferably from about 1.0 to 15 wt %.

Styling Aids

The compositions of the present invention provide good styling attributes, in particular in terms of easy of style, even in the absence of specific styling aids in the conditioner composition or the use of a post-conditioning styling aid such as, for example, a mousse.

The conditioner compositions of the invention may also contain a styling aid. Suitable styling aids are well known to the skilled person and include film-forming polymers and particulate materials. Suitable film-forming polymers are described, for example, in EP 823,252.

Preferred particulate styling aids are those described in the Applicants copending European Patent Application Nos. 01303914.4, 01303915.1, 01303916.9, 01303917.7.

The solid form of the conditioner provides a useful vehicle for delivery of styling aids to the desired part of the hair. For example, when looking for root lift to generate volume, it is preferable to target the styling aid at the roots of the hair as opposed to the tips. If the styling aid is incorporated into the solid, e.g. a stick, conditioner formulation, it is relatively easy to apply and "target" the styling aid at the roots.

When used, a styling aid is suitably present in the compositions of the invention at a level of from 0.1 to 10 wt %, preferably from 0.5 to 5 wt %.

Adjuvants

The compositions of the present invention may also contain adjuvants suitable for hair care. Generally such ingredients are included individually at a level of up to 5, preferably up to 3 wt % of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Mechanical Properties and Product Packages

The compositions of this invention are solid in form and may be firm or soft in appearance. Even a soft solid has an ability to sustain its own shape, for instance if it is removed from a mould without being subjected to shear it will retain its shape for at least 30 seconds, usually longer, at about 20° C.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention is preferably sufficiently rigid that it is not apparently deformable by hand pressure, even though a surface layer will transfer as a film or smear to the hair, and is suitable for use as a stick/bar product in which a quantity of the composition in the form of a stick/bar may be accommodated within a container barrel having an open end at which an end portion of the stick/bar of composition is exposed for use. The opposite end of the barrel is closed.

Generally the container will include a cap for its open end and a component part which is sometimes referred to as an elevator or piston fitting within the barrel and capable of relative axial movement along it. The stick/bar composition is accommodated in the barrel between the piston and the open end of the barrel. The piston is used to urge the stick/bar of composition along the barrel. The piston and stick/bar of composition may be moved axially along the barrel by manual pressure on the underside of the piston using a finger or rod inserted within the barrel. Another possibility is that a rod attached to the piston projects through a slot or slots in the barrel and is used to move the piston and stick/bar. Preferably the container also includes a transport mechanism for moving the piston is comprising a threaded rod which extends axially into the stick/bar through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Of course, if the composition is sufficiently rigid that it is not apparently deformable by reasonable hand pressure, then it may be used as a stick/bar product without the need for a container barrel. This offers the advantages of reducing packaging and costs.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted.

Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick/bar were performed in the barrel. The stick/bar was wound up to project from the open end of the barrel, and then cut off to leave a flat, uniform surface. The needle was carefully lowered to the stick/bar surface, and then a penetration hardness measurement was conducted. This process was carried out at six different points on the stick/bar surface. The hardness reading quoted is the average value of the 6 measurements.

ii) Texture Analyser

The hardness of a softer solid can be measured by using a texture analyser. This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument.

After positioning the sample, the sphere position was adjusted until it was just above the sample surface. Texture expert exceed software was used to generate the subsequent motion profile used in the test method. This profile initially indented the sphere into the sample at an indentation speed of 0.05 mm/s until a designated forte was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in barrels, which had a screw mechanism, or in 15 ml glass jars. For the barrel samples, the stick/bar was wound up until it protruded above the edges of the barrel and then a knife was used to skim the top of the barrel in such a way as to leave a flat uniform surface. The stick/bar was then pushed back into the barrel as far as possible to minimise any mechanical interference resulting from the compliance of the screw mechanism in the pack. Two indents were generally made either side of the screw. The samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{max}[N]}{A_p[mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

Process of Manufacture

The conditioner compositions in solid form can be made by any appropriate method. For example, sticks/bars can be made by simply mixing the components with sufficient heating and agitation to ensure all the components are melted and/or uniformly dispersed (e.g. in the case of any insoluble components). Typically, the compositions are heated to a temperature in the range from 70° C. to 95° C. If any heat sensitive materials are being used, these can be added as the composition cools and mixed in. The heated/warmed solution, still in a mobile state is then poured into a stick/bar mould, which may take the form of a dispensing container, and allowed to cool and solidify.

An alternative method of manufacture of conditioner compositions in solid form is injection moulding. A particularly suitable injection moulding process is described in WO 98/53039 (Unilever). For examples the following injection moulding process has been used to make conditioner bars according to the invention:

1) The full formulation was prepared in a batch mixer by mixing at 80° C. This produced a homogeneous melt which was then cooled to room temperature at which point the product was a waxy solid.
2) The product was broken down into particles sufficiently small to feed, at ambient temperature, into the hopper of a Werner Pfleiderer twin screw co-rotating extruder, with a length to diameter ratio of 28:1 and 30 mm diameter.
3) The extruder was operated at 100 to 150 rpm.
4) The extruder barrel was heated to produce product for injection at 50, 55, 60 and 65° C.
5) The heated, extruded product was fed to a piston injection unit and injected into a bar mould.
6) After the mould was filled it was allowed cool to ambient temperature.
7) The mould was opened and the hair conditioner solid product was removed.

Cooling may be brought about by nothing more than allowing the container and contents to cool. Cooling may be assisted by blowing ambient or even refrigerated air over the moulds/containers and their contents.

The invention will now be further illustrated by the following, non-limiting Examples:

EXAMPLES

Example 1

The following solid conditioner formulations were prepared and packaged in 50 g deodorant-style containers.

| Chemical Name | Trade Name | Active Ingredient wt % | |
|---|---|---|---|
| | | A | B |
| Cetyl trimethyl ammonium chloride | Cetrimonium chloride in water | 12.45 | 12.45 |
| Di hardened tallow dimethyl ammonium chloride | Arquad 2HT-75 PG | 5.475 | 5.475 |
| Ceto-stearyl alcohol | Stenol 16-54 | 44.6 | 44.6 |
| 3:1 mixture of 5-chloro-2-methyl-4-isothiazolin-3-one and 2-methyl-4-isothiazolin-3-one | Kathon CG | 0.00075 | 0.00075 |
| 1,3-dihydroxy-methyl-5,5-dimethylhydantoin | DMDM Hydantoin | 0.2 | 0.2 |
| DC 1403 | Silicone fluid blend | — | 2.0 |
| Perfume | Perfume RH-1883/1 | 1.0 | 1.0 |
| Water | Water | To 100 | To 100 |

In-Homes Panel Test

Up to 20 panellists were recruited as "every other day" washers and so used each test product up to 4 times during a week. The test involved each panellist using both conditioners over a two week period. The panellists used the conditioner in place of their usual conditioner, however they used their own shampoo and styled their hair following their normal routine. The hair was to be washed as normal, the conditioner applied where necessary away from the direct flow of water (i.e. not under a running shower), rubbed into the hair, and then rinsed as normal.

The panellists were divided into three groups. Each panellist was given a 50 g container of product A or B and evaluated the in use properties of the conditioner for a week. Each panellist was then given the other product to test and evaluated the in use properties of that conditioner for a week. At the end of test, the panellists took part in a discussion group and completed a questionnaire.

The results from the questionnaire and discussion groups were as follows:

| | No. of Panellists | |
|---|---|---|
| | A | B |
| Opinion | | |
| Terrible | 1 | 1 |
| Very poor | | 1 |
| Poor | 5 | |
| Fair | 3 | 5 |
| Good | 7 | 3 |

-continued

|  | No. of Panellists | |
| --- | --- | --- |
|  | A | B |
| Very good | 1 | 8 |
| Excellent |  | 1 |
| Suitability |  |  |
| Very suitable | 2 | 2 |
| Unsuitable | 1 | 1 |
| Neither | 2 | 3 |
| Suitable | 5 | 6 |
| Very Suitable | 5 | 7 |
| Purchase intent |  |  |
| Definitely not buy | 1 | 3 |
| Probably not buy | 2 | 2 |
| Not sure | 4 | 3 |
| Probably buy | 5 | 5 |
| Definitely buy | 5 | 6 |
| Achieving style |  |  |
| Extremely difficult | 2 | 2 |
| Very difficult | 2 | 1 |
| Neither | 1 | 4 |
| Very easy | 8 | 9 |
| Extremely easy | 4 | 3 |

Formulation A

The panellists found it difficult to judge how much product to use. The product had to be applied to the hair in sections and was therefore quite time consuming. The conditioner was easy to work through the hair; it "just glided through". Once the product had been worked through the hair, the hair was easy to comb and felt soft and silky. Seven panellists found the product took a long time to rinse out of their hair, the remainder found no difference in rinsing than with a standard conditioner. The rinsed hair felt silky, soft and was easy to wet comb.

Just Conditioner: No Styling Product Used

Four panellists found their hair very easy to style, they were able to achieve volume and height. They thought the conditioner had a styling wax built in to it, as they achieved good curl definition and texture. Nine panellists achieved their normal style. Four panellists found their hair very difficult to style and were unable to achieve any volume or lift. The dry hair was very soft, shiny without flyaway or frizz, it was easy to comb and remained knot/tangle free.

Conditioner Followed by a Styling Product

Several panellists found their hair styled better when they used a mousse as there was less flop and no fluffiness. They were able to achieve volume, body and height and the hair was soft and easy to comb. Three panellists found their hair felt coated and dirty when they had applied a mousse. The remainder commented their hair felt clean and had a subtle healthy shine/sheen.

Intent to Purchase

The product was not like any commercial products the panellists had used.

Twelve panellists would buy the product:

It was portable, economical & could be applied where required. Perceived as a light conditioner that gives styling/control benefits, soft, shiny and tangle free hair.

Three panellists were unsure:

The packaging was perceived as a gimmick and the product was no better than any other hair conditioner. They liked the product but not the packaging; consider good for targeting specific areas.

Five panellists would not buy the product:

Perceived as impractical. A good conditioner that took to long to apply. Made the hair flat and overdressed.

It was noted that three of the panellists who would not buy the product had applied it to towel-dried hair and felt that this influenced their response to the product as it had been difficult to use. They believed the addition of water may have improved the product's performance.

Formulation B

This formulation looked thicker and more concentrated than the formulation A, due to its opaqueness. The product came up easily, it was not sticky, it was softer than the previous product and was easy to apply. The product worked through the wet hair easily. The product gave wet hair a waxy feel and several found their hair took along time to rinse. In addition, they noticed that as the water was added there was a slight foaming. The rinsed hair was soft, silky and easy to wet comb for all bar one panellist, whose hair was knotty.

Just Conditioner: No Styling Product Used

The panellists in two of the groups found the product had made the hair very soft and therefore difficult to style as the hair would not grip the brush. The other group found their hair was easy to style and were able to achieve their desired style. The majority found their dry hair was soft, silky with a healthy shine and was easy to dry comb. Seven panellists found they could leave their hair longer between washes as it was both cleaner feeling and looking, and the hair was not as greasy as with normal conditioners.

Conditioner Followed by a Styling Product

The panellists were able to obtain more control. The hair gripped the brush and so it was easier to achieve the desired style. Several panellists found that when they used a mousse, their hair needed to be washed more often. The hair felt like it had a heavy build up on it and made the hair feel heavy as though not all the conditioner had been rinsed away. The product was more conditioning than a standard conditioner and several panellists felt they would not have to apply the product after every wash to have the level of conditioning they required for their hair.

Intent to Purchase

The product was not like any commercial products the panellists had used.

Six panellists perceived this product as more expensive than a standard conditioner due to the quality and the lasting qualities of the product. Five preferred the formulation A to formulation B (due to the styling benefits when no mousse was used).

Twelve panellists would buy the product:

It left the hair soft bouncy and healthy looking. They had got used to the stick application and felt it had a lot positive properties. Perceived as being a low wastage, easy to carry package, offering the benefit of on the spot application.

Four panellists were unsure:

The packaging was perceived as a gimmick and the product as no better than any other hair conditioner. One panellist would have like longer than a week to evaluate the product.

Four panellists would not buy this product:

Expect a product to enhance the hair not deteriorate it. The hair was left in an unsatisfactory state; dull, coated, frizzy and flyaway.

Example 2

A comparison was made of a conventional liquid conditioner (Suave Peach Essence) against conditioner sticks of formulation A and B from Example 1 in a hair switch test.

7 g/10" Yugo red tie hair switches were ethered then balanced by a panel. Six switches (1–6) were washed by the first shampoo by applying 1 ml of the shampoo along the length of the switch and agitating for 30 seconds, followed by a rinse with warm running water for 30 seconds. Again 1 ml of the same shampoo was placed along the length of the switch and agitated for 30 seconds, followed by a rinse for 1 minute. Switches 1–3 were treated with the conventional liquid conditioner by placing 2 ml of conditioner along the length of the switch and agitating for 1 minute, followed by a rinse for 1 minute. Switches 4–6 were treated with formulation A or B in the same manner. The switches were assessed for their wet conditioning as before. All switches were dried in a circulatory oven at 50° C. for about 2 hours. Finally the switches were assessed for their smoothness, ease of comb, coated feel and lack of flyway when dry. A total of 12 panellists were used, and each compared 6 pairs of switches for five key conditioning attributes: lack of flyaway, ease of dry comb, dry smoothness, ease of wet comb and wet smoothness. The total no. of 'favoured' switches for each application were added up and expressed as a percentage.

Formulation A (without silicone) beat the conventional liquid conditioner on all five attributes, the wins on flyaway, ease of dry comb and dry smoothness being significant at 95% confidence.

Formulation B (with silicone) beat the conventional liquid conditioner on four attributes, and scored identically on flyaway. The wins on dry smoothness, ease of wet comb and wet smoothness being significant at 95% confidence.

What is claimed is:

1. A hair conditioner composition in solid form comprising
   (i) at least 5 wt. % cationic surfactant, and
   (ii) at least 20 wt. % fatty alcohol material
   wherein the composition contains less than 80 wt. % water, the composition having a shape which is a stick or bar.

2. A composition according to claim 1, in which the water content is less than 60 wt. %.

3. A composition according to claim 1 or claim 1, in which the cationic surfactant is present in an amount of at least 12 wt. %.

4. A composition according to claim 1, in which the cationic surfactant is selected from cetrimonium chloride, behenyltrimonium chloride, PEG-2 oleamonium chloride, di-hardened tallow dimethylammonium chloride, distearyldimethylammonium chloride and mixtures thereof.

5. A composition according to claim 1, in which the fatty alcohol material is a C8-22 fatty alcohol.

6. A composition according to claim 1, in which weight ratio of fatty alcohol material to cationic surfactant is in the range from 10:1 to 1:10.

7. A composition according to claim 1, further comprising 0.01 to 25 wt. % of a cationic polymer.

8. A composition according to claim 1, further comprising a conditioning agent selected from silicone conditioning agents and non-silicone oily conditioning agents.

9. A composition according to claim 8, in which the silicone conditioning agent is present at a level of from 0.5 to 25 wt. %.

10. A composition according to claim 1, which further comprises from 0.1 to 10 wt. % of a styling aid selected from film-forming polymers and particulate materials.

11. A composition according to claim 1, which has a penetration of less than 30 mm.

12. A composition according to claim 1, in which weight ratio of fatty alcohol material to cationic surfactant is in the range from 7:1 to 1:1.

13. A composition according to claim 1, in which weight ratio of fatty alcohol material to cationic surfactant is in the range from 5:1 to 2:1.

14. A composition according to claim 1, in which the cationic surfactant is present in an amount of at least 8 wt. %.

15. A composition according to claim 1, wherein the fatty alcohol material is present in an amount of at least 40 wt. %.

* * * * *